United States Patent [19]

Cognigni et al.

[11] Patent Number: 4,614,815

[45] Date of Patent: Sep. 30, 1986

[54] PROCESS FOR PRODUCING DIESTERDIAMIDES

[75] Inventors: Franco Cognigni, Pisticci; Armando Mariano, Pisticci Scalo, both of Italy

[73] Assignee: Anic S.p.A., Palermo, Italy

[21] Appl. No.: 385,529

[22] Filed: Jun. 7, 1982

Related U.S. Application Data

[63] Continuation of Ser. No. 171,090, Jul. 22, 1980, abandoned.

[30] Foreign Application Priority Data

Sep. 10, 1979 [IT] Italy ............................... 25570 A/79

[51] Int. Cl.[4] .............................................. C07C 67/00
[52] U.S. Cl. ..................................... 560/88; 528/292; 560/37; 560/169; 560/171; 560/196
[58] Field of Search .................. 560/37, 88, 169, 171, 560/196; 528/292

[56] References Cited

U.S. PATENT DOCUMENTS 2,839,508 6/1958 Williams et al. .
2,848,439 8/1958 Reynolds et al. .
2,851,443 9/1958 Williams et al. .
2,856,385 10/1958 Van Den Berghe et al. .
2,861,055 11/1958 Williams et al. .
2,925,405 2/1960 Loakso et al. .

FOREIGN PATENT DOCUMENTS 1365952 9/1974 United Kingdom .

*Primary Examiner*—Natalie Trousof
*Assistant Examiner*—Vera C. Clarke
*Attorney, Agent, or Firm*—Morgan & Finnegan

[57] ABSTRACT

Process for preparing diesterdiamides, consisting of reacting a diester with a diamine under wet conditions in the presence of suitable solvents and catalysts, to give the diester diamide, together with an ester salt derivative as impurity. The reaction product is then filtered to give a diesterdiamide cake and a mother solution of the reagents which also contains the solvent, the catalyst and the ester salt product. The cake is washed with a solvent of the ester salt, which also dissolves the reagents and catalysts. The mother solution and wash solution are then distilled, the two fractions obtained being recycled to the synthesis and to the wash.

3 Claims, No Drawings

PROCESS FOR PRODUCING DIESTERDIAMIDES

This is a continuation of application Ser. No. 171,090, filed July 22, 1980, now abandoned.

This invention relates to a process for producing diesterdiamides.

The reaction between a diester and a diamine, where the diester is present in excess in accordance with Italian Pat. Nos. 908843 and 908844, leads to the formation of diesterdiamides, which are useful for the preparation of polymers. In particular, the polymers derived from the reaction between the glycols hexanediol and/or dodecanediol and the diesterdiamides, N,N''-p-carboalkoxybenzoyldodecamethylenediamine and/or N,N'-p-carboalkoxybenzoylhexamethylenediamine also find application in the production of fibres similar to silk (Italian Pat. Nos. 908843 and 908844 and U.S. Pat. No. 2,848,439).

The process for preparing the said diesterdiamides by reacting the reagents in solvent solutions (mixtures of aliphatic and/or aromatic and/or cycloaliphatic hydrocarbons with alcohols) is described in the aforesaid Italian patents, and comprises the use of anhydrous solvents and pure reagents, with a metal alcoholate as catalyst. However, in practice it is extremely burdensome to operate with solvents and reagents which are totally free from water. In this respect, while it is easy to obtain anhydrous hydrocarbons and preserve them as such, the same is not true of alcohols and diamines, and even esters such as fibre grade dimethylterephthalate always contain a small amount of water.

This means that in industrial practice there is the formation of a by-product of the diesterdiamide synthesis in the form of an ester salt derived from the diester used, as the result of hydrolysis by the hydroxide corresponding to the metal alcoholate used as catalyst, in accordance with the scheme:

$$Me^+RO^- + H_2O \rightleftharpoons ROH + Me^+OH^-$$
$$Me^+OH^- + R'(COOR)_2 \rightarrow R'(COOR)COO^-Me^+ + ROH$$

where Me indicates the alcoholate metal and R is an alkyl group with a low number of carbon atoms, such as a methyl group, and R' is a bivalent alkyl radical containing 2 to 30 carbon atoms. Depending on the nature of the solvents used in the synthesis, the composition of the solvent mixture, the nature of the metal (preferably alkaline) present in the catalytic solution, and the moisture content of the reagents and solvents, the quantity of ester salt formed can either be less than or greater than its solubility limit, in which latter case it coprecipitates with the product.

This by-product cannot be tolerated in the subsequent polymer production stages, and even less so in the production of the fibres obtained from the polymer, because it leads to rapid blocking of the spinnerets, spinning difficulties (fine floss) and drawing difficulties (burring), decay of the mechanical characteristics of the filaments produced and of their brightness, low resistance to light by the manufactured articles, and a worsening of the thermo-oxidative stability of the polymer.

The ester salt could be removed from the product after filtering the precipitates by subsequently washing these latter with suitable solvents of the ester salt, then resuspending them (under hot conditions or at ordinary temperature) followed by filtration.

However, it is hardly practical to wash the product followed by resuspension and filtration, it being preferable and more economical to directly wash the crude product cake. However, in practice there is the problem of reusing the mother filtration and/or wash solutions (because they contain the excess reagents and catalyst) without expensive purification.

The solubility characteristics of the ester salt together with the fact that the make-up reagents and solvents are not completely anhydrous mean that the by-product accumulates progressively in the mother filtration and/or wash solutions (where these are completely re-used) until its solubility limit is reached, when it then coprecipitates with the product to make it more difficult to remove by washing the cake. It has now been surprisingly found possible to remove the ester salt and at the same time recover nearly the whole of the reagents, solvents and catalysts in the mother filtration and/or wash liquors by simply carrying out a suitable distillation of the solvent and ester salt.

The process according to the present invention comprises reacting the diester and diamine in the presence of solvents and catalysts under wet conditions such as to form the required diesterdiamide together with an impurity constituted by an ester salt derived from the diester used due to hydrolysis by the hydroxide corresponding to the metal alcoholate used as catalyst, then filtering the diesterdiamide and recovering the mother solution containing the reagents, solvents, catalysts and ester salt, washing the diesterdiamide with a solvent in which the diesterdiamide is insoluble but in which the reagents, catalyst and corresponding ester salt are soluble, then distilling the mother solution and/or wash solution either together or separately, removing part of the ester salt solvent until most of said ester salt has precipitated while at the same time maintaining the catalyst in solution, then finally recycling the mother solution and/or the wash solution depleted of the ester salt solvent back to the diesterdiamide synthesis.

The solvent used for the ester salt, reagents and catalyst is preferably the same type of alcohol used as solvent during the synthesis of the diesterdiamide.

By way of example, the following table gives the solubilities of lithium methylate, sodium methylate, lithium methylterephthalate (Li Te) and sodiumterephthalate (Na Te) in various mixtures of toluene and methanol (tol/met)

|                    | Solubility meq/liter | | | |
| --- | --- | --- | --- | --- |
| Tol/met by volume | Li OCH$_3$ | Li Te | Na OCH$_3$ | Na Te |
| 65/35 | 300 | 52   | 300 | 22  |
| 75/25 | 200 | 31.5 | 200 | 11  |
| 80/20 | 100 | 22.8 | 80  | 8.5 |
| 85/15 | 75  | 15   | 50  | 6   |
| 90/10 | 40  | 7    | 33  | 3.5 |
| 95/5  | 23  | 2    | 19  | 1.5 |

The solubility values shown were determined at 60° C. both in the presence of 200 g/l of anhydrous dimethylterephthalate and in the solvents alone, without any significant difference between the two conditions.

With regard to the solvents for carrying out the diesterdiamide formation reaction, these are advantageously chosen from mixtures of alcohols and hydrocarbons, and in particular preferably methanol, ethanol, isopropanol, propanol, butanol and isobutanol for the alcohols, and toluene, benzene, hexane, heptane and cyclohexane for the hydrocarbons.

The esters used for the diesterdiamide synthesis are chosen preferably from dimethylterephthalate, dimethylisophthalate, dibutylterephthalate, diethylterephthalate and diethylsuccinate. The catalysts are generally alcoholates of metals, particularly alkaline or alkaline earth metals, and preferably Li and Na. The solubility of the ester salt must be reduced by removing the solvent, to the point at which after separating the part made insoluble there remains in the mother liquors an amount only such that the solubility limit of the ester salt cannot be attained during the subsequent synthesis reaction, given the water content of the make-up material, so that the product remains easily purifiable by washing.

The ester salt made insoluble by partial removal of the alcohol from the mother liquors can be separated by the usual hot solid-liquid separation methods out of contact with air (centrifuging, filtration and pressure, vacuum, decantation etc.).

Some examples are given hereinafter for the purpose of better illustrating the invention, but they are not to be considered as limiting thereof.

In the examples which follow the term "6NT" has been used to designate N,N'-di(p-carbomethoxybenzoyl)hexamethylenediamine. As known in the prior art, this is the diesterdiamide formed by the reaction of 1,6-hexamethylenediamine with at least two molar equivalents of dimethylterephthalate, in the presence of a lithium alcoholate catalyst and in an alcohol-hydrocarbon solvent medium.

EXAMPLE 1

779 kg of toluene ($H_2O = 10$ ppm), 79 kg of methanol ($H_2O = 70$ ppm), 230 kg of DMT (dimethylterephthalate) ($H_2O = 200$ ppm) and 25 equivalents of Li $OCH_3$ are fed into a reactor having a volume of 2 $m^3$ fitted with a stirrer and a $N_2$ supply. The mixture is heated to 70° C., and 42 kg of hexamethylenediamine ($H_2O = 800$ ppm) are fed to form the 6NT. The methanol developed by the reaction is simultaneously distilled off as an azeotrope with toluene.

At the end of the reaction, the mass has the following composition: Toluene 70.3%; Methanol 7.2%; DMT 8.63%; 6NT 13.9%; Li $OCH_3$ 19 eq; (Lithium terephthalate 6 eq); and the 6NT is separated by filtration through a filter under pressure and washed on the filter with 600 liters of a mixture of methanol and toluene having a volume composition of 75/25 $H_2O = 40$ ppm).

The wet monomer discharged from the filter is dried at 100° C. under ordinary pressure in a $N_2$ stream, and has the following characteristics: M.P. 232° C.; N 6.4%; C 65.4%; H 6.5%; lithium = 3 meq/kg (Li Te = 0.05%).

The mother and wash liquors are combined and have the following composition: DMT 7.2%; Toluene 65.8%; Methanol 27%; Li $OCH_3$ = 17 eq; Li Te = 8 eq.

The solvents used for washing (with the exception of the amount remaining impregnated in the cake) are stripped in an evaporator comprising a packed column to give a residue in the form of a mass of about 950 kg having the following composition: DMT 10%; Toluene 81.7%; Methanol 8.3%; and containing the lithium compounds.

EXAMPLE 2

The residue of example 1 is recycled integrally to the reactor for the synthesis of the 6NT, under the same conditions as in example 1, after adding the compositions.

At the end of the reaction, the mass has approximately the same composition as in example 1, and contains 21 eq of Li $OCH_3$ and 12 eq of lithium terephthalate.

On carrying out the filtration and wash operations in an identical manner to example 1, a dry monomer is obtained having a lithium content of 25 meq/kg (Li Te = 0.45%), while the mixture of mother and wash liquors contains about 19 equivalents of Li $OCH_3$ and 11 equivalents of lithium terephthalate. After stripping the wash solvent, the composition of the residue is approximately equal to that of the residue of example 1.

EXAMPLE 3

The residue of example 2 having the following composition: DMT 10.1%; Toluene 81.5%; Methanol 8.4%; Li $OCH_3$ 19 equivalents. Lithium terephthalate 11 equivalents is stripped of the solvent (methanol/toluene of 75/25 composition) until the following composition is obtained: DMT 10.6%; Toluene 84%; Methanol 5.4%; Li $OCH_3$ = 21 meq/kg. Lithium terephthalate = 12 meq/kg, which is then passed at 60° C. through a centrifugal decanter to give 900 kg of a mass having a composition equal to the initial composition (Li $OCH_3$ 21 meq/kg, Li Te 3.4 mg/kg).

After adding 135 kg of DMT, 23 kg of toluene, 30 kg of methanol and 6 equivalents of Li $OCH_3$ to this material, hexamethylenediamine (42 kg) was added for a new synthesis of 6NT as in example 1, to give a mass of the following composition: Toluene 70.15%; Methanol 7.2%; DMT 8.8%; 6NT 13.9%; Li $OCH_3$ 21 equivalents; Li Te 7.1 equivalents.

A 6NT monomer having a lithium content of less than or equal to 3 meq/kg was recovered from this mass by filtration, washing and drying.

We claim:

1. In a process for the preparation of a diesterdiamides comprising the step of reacting under non-anhydrous conditions a diamine with at least two molar equivalents of a diester, in the presence of a sodium or a lithium alcoholate catalyst and in a solvent selected from mixtures of alcohols and hydrocarbons to form the desired diesterdiamide and, as a by-product, an ester salt derived from the diester starting material, and further comprising the step of collecting on a filter the precipitate, consisting mainly of the diesterdiamide product, and collecting the filtrate consisting of unreacted starting materials, solvent, catalyst and said diester salt, the improvement which comprises washing the diesterdiamide cake with a solvent mixture of the same type used in the reaction mixture, combining said wash solution with the previous filtrate, reducing the volume of the resulting solution by distillation, removing therefrom the ester salt which precipitates, and recovering the unreacted starting materials, solvent and catalyst for reutilization in the initial reaction.

2. The process of claim 1 wherein the alcohol used in the solvent mixture is methanol.

3. The process of claim 1 wherein the hydrocarbon used in the solvent mixture is toluene.

* * * * *